(12) United States Patent
Takahata et al.

(10) Patent No.: US 7,152,582 B2
(45) Date of Patent: Dec. 26, 2006

(54) GASOLINE TYPE IDENTIFYING SYSTEM AND METHOD FOR IDENTIFYING GASOLINE TYPE

(75) Inventors: Takayuki Takahata, Ageo (JP); Toshiaki Kawanishi, Ageo (JP); Kiyoshi Yamagishi, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 0 days.

(21) Appl. No.: 10/527,302

(22) PCT Filed: Sep. 10, 2003

(86) PCT No.: PCT/JP03/11569

§ 371 (c)(1), (2), (4) Date: Mar. 9, 2005

(87) PCT Pub. No.: WO2004/025287

PCT Pub. Date: Mar. 25, 2004

(65) Prior Publication Data

US 2006/0011170 A1 Jan. 19, 2006

(30) Foreign Application Priority Data

Sep. 10, 2002 (JP) ............................. 2002-264543

(51) Int. Cl.
*F02P 5/15* (2006.01)
*G01N 25/18* (2006.01)
*F02D 45/00* (2006.01)

(52) U.S. Cl. .............................. 123/406.12; 73/61.46; 123/48 R; 123/78 R; 123/494

(58) Field of Classification Search ................ 123/1 A, 123/48 R, 78 R, 406.12, 406.19, 494; 73/35.02, 73/116, 117.2, 117.3, 61.46
See application file for complete search history.

(56) References Cited

U.S. PATENT DOCUMENTS

| 5,191,869 | A | * | 3/1993 | Kamioka et al. | ............ | 123/494 |
| 5,345,908 | A | * | 9/1994 | Nishimura et al. | .... | 123/339.14 |
| 6,250,137 | B1 | * | 6/2001 | Takahashi et al. | ......... | 73/64.53 |
| 6,318,152 | B1 | * | 11/2001 | Hagihara et al. | .......... | 73/35.02 |

FOREIGN PATENT DOCUMENTS

| JP | 3-262949 A | 11/1991 |
| JP | 4-178550 A | 6/1992 |
| JP | 11-153561 A | 6/1999 |
| WO | WO 01/44761 A | 6/2001 |

\* cited by examiner

*Primary Examiner*—T. M. Argenbright
(74) *Attorney, Agent, or Firm*—The Webb Law Firm

(57) ABSTRACT

The types of gasolines having different distillation characteristics and various compositions are identified accurately and rapidly. A pulse voltage is applied for a predetermined time to a liquid type identifying sensor heater including a heater and an identifying liquid temperature sensor provided in the vicinity of the heater. Then, a gasoline to be identified is heated by the heater, and a liquid type is identified with a voltage output difference V0 corresponding to a temperature difference between an initial temperature and a peak temperature in the identifying liquid temperature sensor.

35 Claims, 15 Drawing Sheets

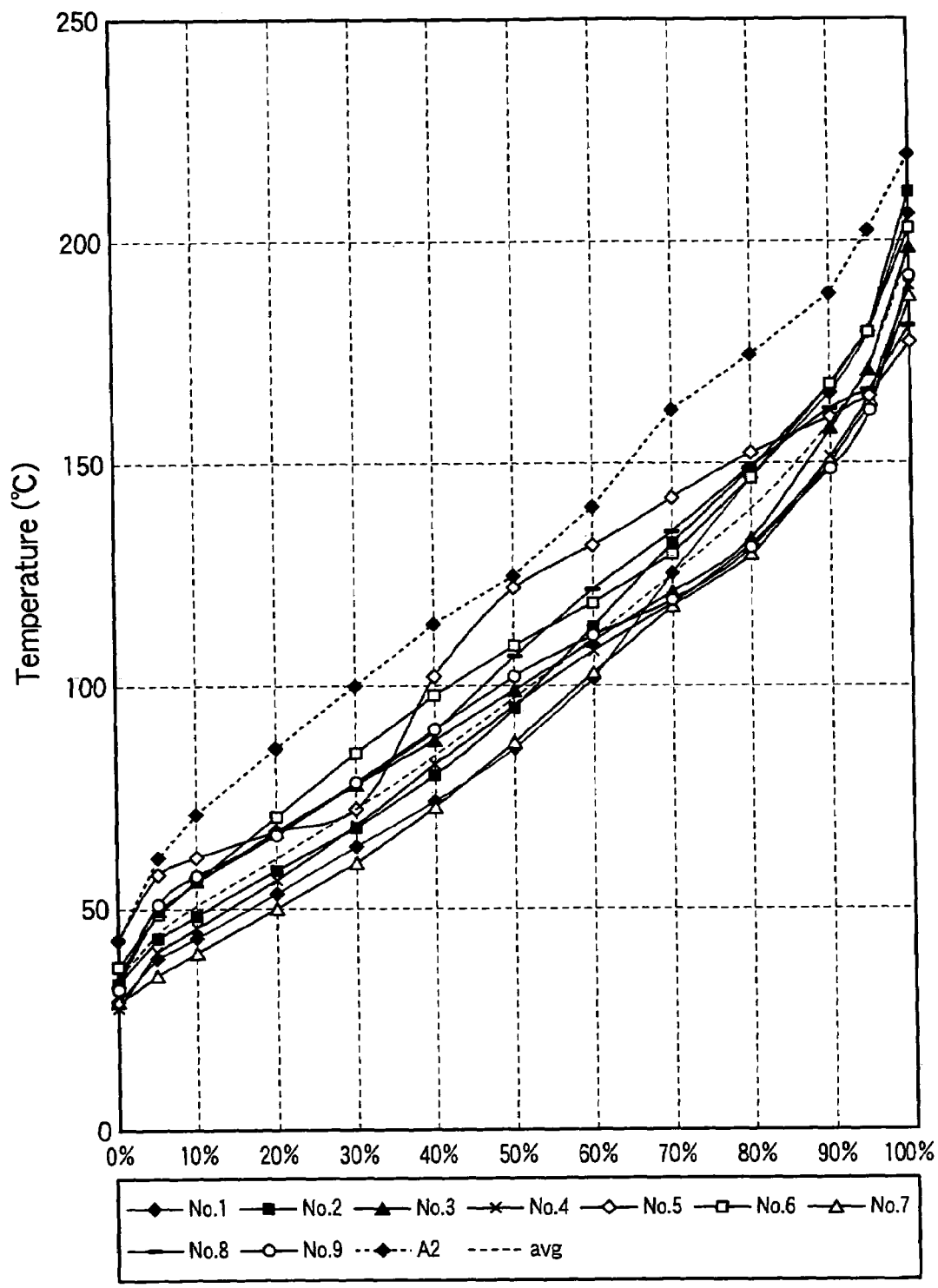

GASOLINE TYPE IDENTIFYING SYSTEM AND METHOD FOR IDENTIFYING GASOLINE TYPE

TECHNICAL FIELD

The present invention relates to an apparatus and method for identifying the liquid type of a gasoline.

BACKGROUND ART

Conventionally, the exhaust gas of a car contains pollutants such as unburned hydrocarbon (HC), an NOx gas and an SOx gas. In order to reduce the pollutants, therefore, S in a gasoline is removed from the SOx or unburned HC is burned by a catalyst, for example.

More specifically, as shown in FIG. 14, a car system 100 takes air in through an automatic element (filter) 102 and feeds the air into an engine 106 through an airflow sensor 104. Moreover, the car system 100 feeds a gasoline in a gasoline tank 108 into the engine 106 through a gasoline pump 110.

Based on the result of the detection of an A/F sensor 112, the injection of the fuel in the engine 106 is controlled by a fuel injection control device 114 in order to have a predetermined theoretical air fuel ratio.

For an exhaust gas fed from the engine 106, hydrocarbon (HC) in the exhaust gas is burned by a catalytic device 116 and is then discharged as the exhaust gas through an oxygen concentration sensor 118.

In such a car system, gasolines sold all over the world include various gasolines having different distillation characteristics (different easinesses of evaporation) as shown in FIG. 15.

More specifically, FIG. 15 shows the distillation characteristics of gasolines, illustrating a relationship between a percentage and a temperature. Namely, for example, an axis of abscissa of 50% (T50) indicates a temperature at which 50% of each gasoline evaporates.

As shown in FIG. 15, for example, a gasoline A2 represents the heaviest gasoline (which rarely evaporates) and a gasoline No. 7 represents the lightest gasoline (which easily evaporates) with respect to a standard gasoline No. 3.

As shown in the following Table 1, accordingly, for example, in the case in which the heavier gasoline A2 is used in a car regulated to have a theoretical air fuel ratio with the standard gasoline No. 3, the amount of HC in an exhaust gas is small and a torque becomes insufficient, particularly, at time of engine starting in which an engine and a catalytic device do not warm up.

To the contrary, in the case in which the lighter gasoline No. 7 is used, the torque is insufficient and the theoretical air fuel ratio is exceeded. Furthermore, in this case, and the amount of the HC in the exhaust gas is increased, particularly, at time of the engine starting in which the engine and the catalytic device do not warm up, which is not preferable because an environment is greatly influenced.

TABLE 1

| Regulated gasoline | Used gasoline | Torque | Exhaust gas (HC) |
|---|---|---|---|
| No. 3 | No. 3 | ○ | ○ |
| No. 3 | No. 2 | X | ○ |
| No. 3 | No. 7 | ○ | X |

The present inventors have proposed a fluid identifying method for causing a heating member to generate heat by carrying electricity, heating a temperature detector through the heat generation, thermally influencing a heat transfer from the heating member to the temperature detector through a fluid to be identified, and distinguishing the type of the identified fluid based on an electrical output corresponding to the electric resistance of the temperature detector, thereby periodically carrying the electricity to the heating member in Japanese Laid-Open Patent Publication No. 11(1999)-153561 (particularly see paragraphs [0042] to [0049]).

In the fluid identifying method, however, it is necessary to periodically carry the electricity to the heating member (in a multipulse). For this reason, a long time is required for the identification so that it is hard to identify a fluid instantaneously. In this method, moreover, it is possible to identify a fluid based on a central value for substances having very different characteristics such as water, air and oil. However, it is hard to identify the gasolines having very close characteristics to each other accurately and rapidly.

In consideration of such circumstances, it is an object of the present invention to provide an apparatus and method for identifying the liquid type of a gasoline which can identify the types of gasolines having different distillation characteristics and various compositions accurately and rapidly.

Moreover, it is an object of the present invention to provide an apparatus and method for identifying the liquid type of the gasoline of a car using the apparatus and method for identifying the liquid type of a gasoline.

Furthermore, it is an object of the present invention to provide an apparatus and method for reducing the exhaust gas of a car using the apparatus and method for identifying the liquid type of a gasoline which can efficiently reduce the exhaust gas and can enhance a mileage.

SUMMARY OF THE INVENTION

The present invention has been made to solve the problems and to attain the objects in the prior art described above, and provides an apparatus for identifying a liquid type of a gasoline, comprising:

a gasoline liquid type identifying chamber for causing an identified gasoline introduced into a liquid type identifying apparatus body to stay temporarily;

a liquid type identifying sensor heater provided in the gasoline liquid type identifying chamber; and a liquid temperature sensor provided in the gasoline liquid type identifying chamber apart from the liquid type identifying sensor heater at a constant interval;

the liquid type identifying sensor heater including a heater and an identifying liquid temperature sensor provided in the vicinity of the heater, and the apparatus further comprising an identification control portion;

the identification control portion being constructed that a pulse voltage is applied to the liquid type identifying sensor heater for a predetermined time, and the identified gasoline staying temporarily in the gasoline liquid type identifying chamber is heated by the heater and the liquid type is identified with a voltage output difference V0 corresponding to a temperature difference between an initial temperature and a peak temperature in the identifying liquid temperature sensor.

Moreover, the present invention provides a method for identifying a liquid type of a gasoline, comprising the steps of:

applying a pulse voltage for a predetermined time to a liquid type identifying sensor heater including a heater and an identifying liquid temperature sensor provided in the vicinity of the heater;

heating an identified gasoline by the heater; and identifying the liquid type with a voltage output difference V0 corresponding to a temperature difference between an initial temperature and a peak temperature in the identifying liquid temperature sensor.

By such a structure, it is sufficient that the pulse voltage is applied for the predetermined time. Consequently, it is possible to identify the type of a gasoline accurately and rapidly through heating for a short time without carrying out the heating to such a temperature as to ignite the gasoline.

More specifically, there are utilized the correlation of the kinetic viscosity of the gasoline with a sensor output, a natural convection, and furthermore, an applied voltage having one pulse. Therefore, it is possible to identify the type of the gasoline accurately and rapidly.

Furthermore, the present invention is characterized in that the voltage output difference V0 is equal to a voltage difference between an average initial voltage V1 obtained by sampling an initial voltage before application of the pulse voltage at a predetermined number of times and an average peak voltage V2 obtained by sampling a peak voltage after the application of the pulse voltage at a predetermined number of times, that is, $$V0 = V2 - V1.$$

By such a structure, it is possible to accurately obtain the voltage output difference V0 based on the average value of the sampling at the predetermined number of times for the applied voltage having one pulse. Consequently, it is possible to identify the type of a gasoline accurately and rapidly.

In addition, the present invention provides the apparatus for identifying a liquid type of a gasoline, wherein the identification control portion identifies a type of a gasoline with the voltage output difference V0 obtained for the identified gasoline, which is based on calibration curve data to be a correlation of a voltage output difference with a temperature for a predetermined reference gasoline prestored in the identification control portion.

Moreover, the present invention provides the method for identifying a liquid type of a gasoline, wherein a type of a gasoline is identified with the voltage output difference V0 obtained for the identified gasoline, based on calibration curve data to be a correlation of a voltage output difference with a temperature for a predetermined reference gasoline which is prestored.

By such a structure, the type of a gasoline is identified with the voltage output difference V0 obtained for the identified gasoline based on the calibration curve data to be the correlation of the voltage output difference with the temperature for the predetermined reference gasoline which is prestored. Therefore, it is possible to identify the type of the gasoline more accurately and rapidly.

Furthermore, the present invention provides the apparatus for identifying a liquid type of a gasoline, wherein the identification control portion correlates a liquid type voltage output Vout for the voltage output difference V0 at a measuring temperature of the identified gasoline with an output voltage for a voltage output difference at a measuring temperature for a predetermined threshold reference gasoline and thus carries out a correction.

In addition, the present invention provides the method for identifying a liquid type of a gasoline, wherein a liquid type voltage output Vout for the voltage output difference V0 at a measuring temperature of the identified gasoline is correlated with an output voltage for a voltage output difference at a measuring temperature for a predetermined threshold reference gasoline and is thus corrected.

By such a structure, the liquid type voltage output Vout for the voltage output difference V0 at the measuring temperature of the identified gasoline is correlated with the output voltage for the voltage output difference at the measuring temperature for the predetermined threshold reference gasoline and is thus corrected. Consequently, it is possible to eliminate the influence of the temperature on the voltage output difference V0, thereby giving the correlation of the liquid type voltage output Vout with the characteristics of the gasoline more accurately. Thus, it is possible to identify the type of the gasoline further accurately and rapidly.

Moreover, the present invention is characterized in that the liquid type identifying sensor heater is a laminated liquid type identifying sensor heater in which a heater and an identifying liquid temperature sensor are laminated through an insulating layer.

By such a structure, a mechanism portion for carrying out a mechanical operation is not present. Therefore, an operation failure is not caused by a deterioration with the passage of time, foreign matters in the gasoline or the like. Thus, it is possible to identify the liquid type of the gasoline accurately and rapidly.

In addition, the sensor portion can be constituted to be very small-sized. Consequently, it is possible to identify the liquid type of the gasoline accurately with a very excellent thermal responsiveness.

Furthermore, the present invention is characterized in that the heater and the identifying liquid temperature sensor in the liquid type identifying sensor heater are constituted to come in contact with the identified gasoline through a metallic fin, respectively.

By such a structure, the heater and the identifying liquid temperature sensor in the liquid type identifying sensor heater do not directly come in contact with the identified gasoline. Therefore, an operation failure is not caused by a deterioration with the passage of time, foreign matters in the gasoline or the like. Thus, it is possible to identify the liquid type of the gasoline accurately and rapidly.

Moreover, the present invention is characterized in that the liquid temperature sensor is constituted to come in contact with the identified gasoline through the metallic fin.

By such a structure, the liquid temperature sensor does not directly come in contact with the identified gasoline.

Therefore, an operation failure is not caused by a deterioration with the passage of time, foreign matters in the gasoline or the like. Thus, it is possible to identify the liquid type of the gasoline accurately and rapidly.

In addition, the present invention provides an apparatus for identifying a liquid type of a gasoline of a car, comprising:

any of the apparatuses for identifying a liquid type of a gasoline described above which is provided in a gasoline tank or on an upstream side or a downstream side of a gasoline pump.

Furthermore, the present invention provides a method for identifying a liquid type of a gasoline of a car, comprising the step of:

identifying a type of a gasoline in a gasoline tank or on an upstream side or a downstream side of a gasoline pump by using any of the methods for identifying a liquid type of a gasoline described above.

By such a structure, it is possible to identify the type of a gasoline accurately and rapidly in a car.

In addition, the present invention provides an apparatus for reducing an exhaust gas of a car, comprising:

any of the apparatuses for identifying a liquid type of a gasoline described above which is provided in a gasoline tank or on an upstream side or a downstream side of a gasoline pump; and an ignition timing control device for regulating an ignition timing based on a type of the gasoline which is identified by the apparatus for identifying a liquid type of a gasoline.

Moreover, the present invention provides a method for reducing an exhaust gas of a car, comprising the steps of:

identifying a type of a gasoline in a gasoline tank or on an upstream side or a downstream side of a gasoline pump by using any of the methods for identifying a liquid type of a gasoline described above, and regulating an ignition timing based on the type of the gasoline which is identified by the apparatus for identifying a liquid type of a gasoline.

By such a structure, an ignition timing can be regulated based on the result of the identification of the type of the gasoline. Therefore, it is possible to obtain a proper ignition timing corresponding to the type of the gasoline.

Accordingly, it is also possible to reduce the amount of HC in an exhaust gas and to enhance a mileage without decreasing a torque, particularly, at time of engine starting in which an engine and a catalytic device do not warm up.

Furthermore, the present invention provides an apparatus for reducing an exhaust gas of a car, comprising:

any of the apparatuses for identifying a liquid type of a gasoline described above which is provided in a gasoline tank or on an upstream side or a downstream side of a gasoline pump; and a gasoline compression control device for regulating a compressibility of the gasoline based on a type of the gasoline which is identified by the apparatus for identifying a liquid type of a gasoline.

Moreover, the present invention provides a method for reducing an exhaust gas of a car, comprising the steps of:

identifying a type of a gasoline in a gasoline tank or on an upstream side or a downstream side of a gasoline pump by using any of the methods for identifying a liquid type of a gasoline described above, and regulating a compressibility of the gasoline based on the type of the gasoline which is identified by the apparatus for identifying a liquid type of a gasoline.

By such a structure, the compressibility of the gasoline can be regulated based on the result of the identification of the type of the gasoline. Therefore, it is possible to obtain a proper compressibility of the gasoline corresponding to the type of the gasoline.

Accordingly, it is also possible to reduce the amount of HC in an exhaust gas and to enhance a mileage without decreasing a torque, particularly, at time of engine starting in which an engine and a catalytic device do not warm up.

BRIEF DESCRIPTION OF THE DRAWINGS

FIG. 15 is a graph showing the distillation characteristics of a gasoline.

DETAILED DESCRIPTION OF THE INVENTION

Embodiments (examples) of the present invention will be described below in more detail with reference to the drawings.

Figure 1:
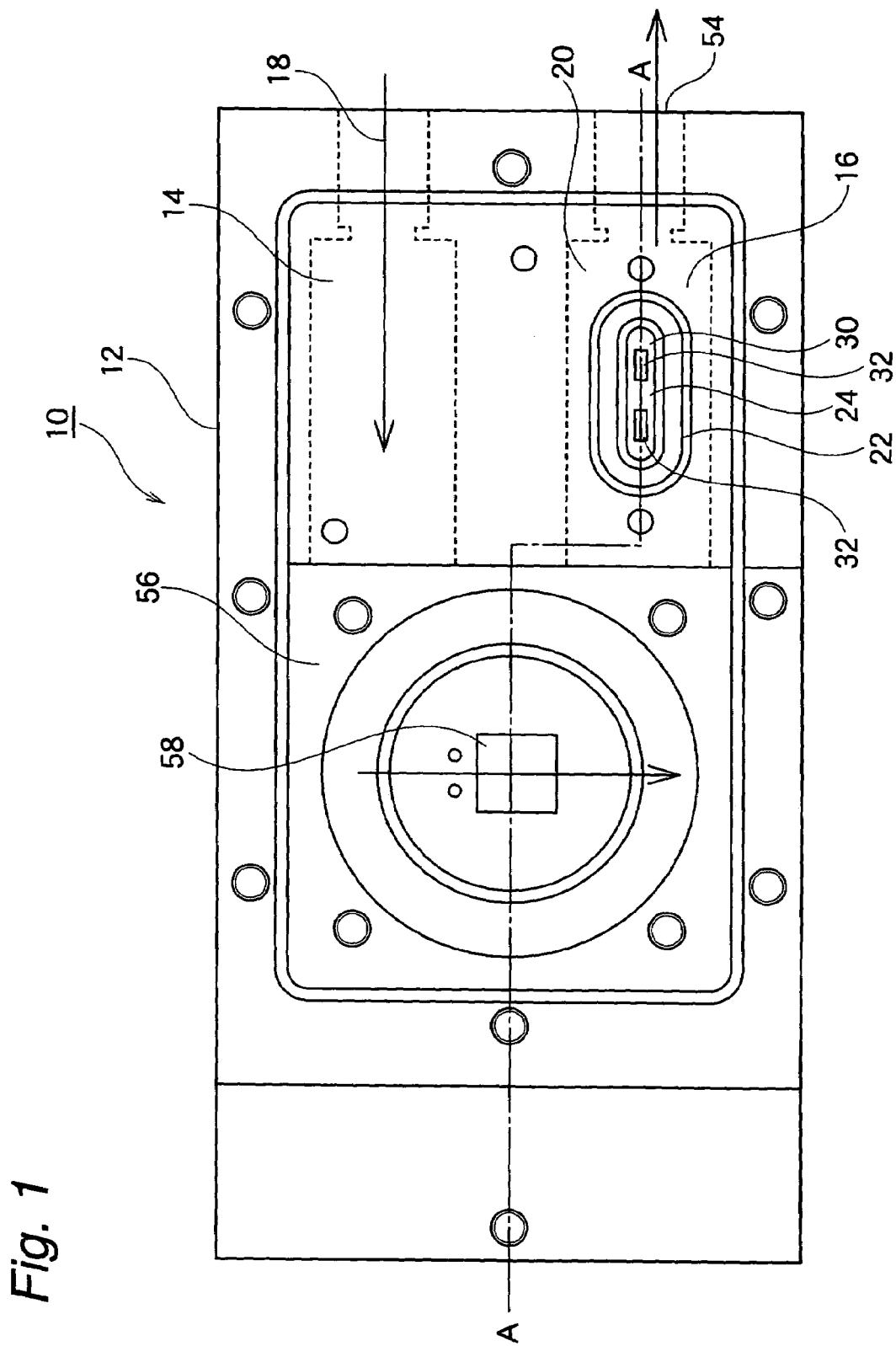
FIG. 1 is a schematic top view showing an example of an apparatus for identifying the liquid type of a gasoline according to the present invention.
Figure 2:
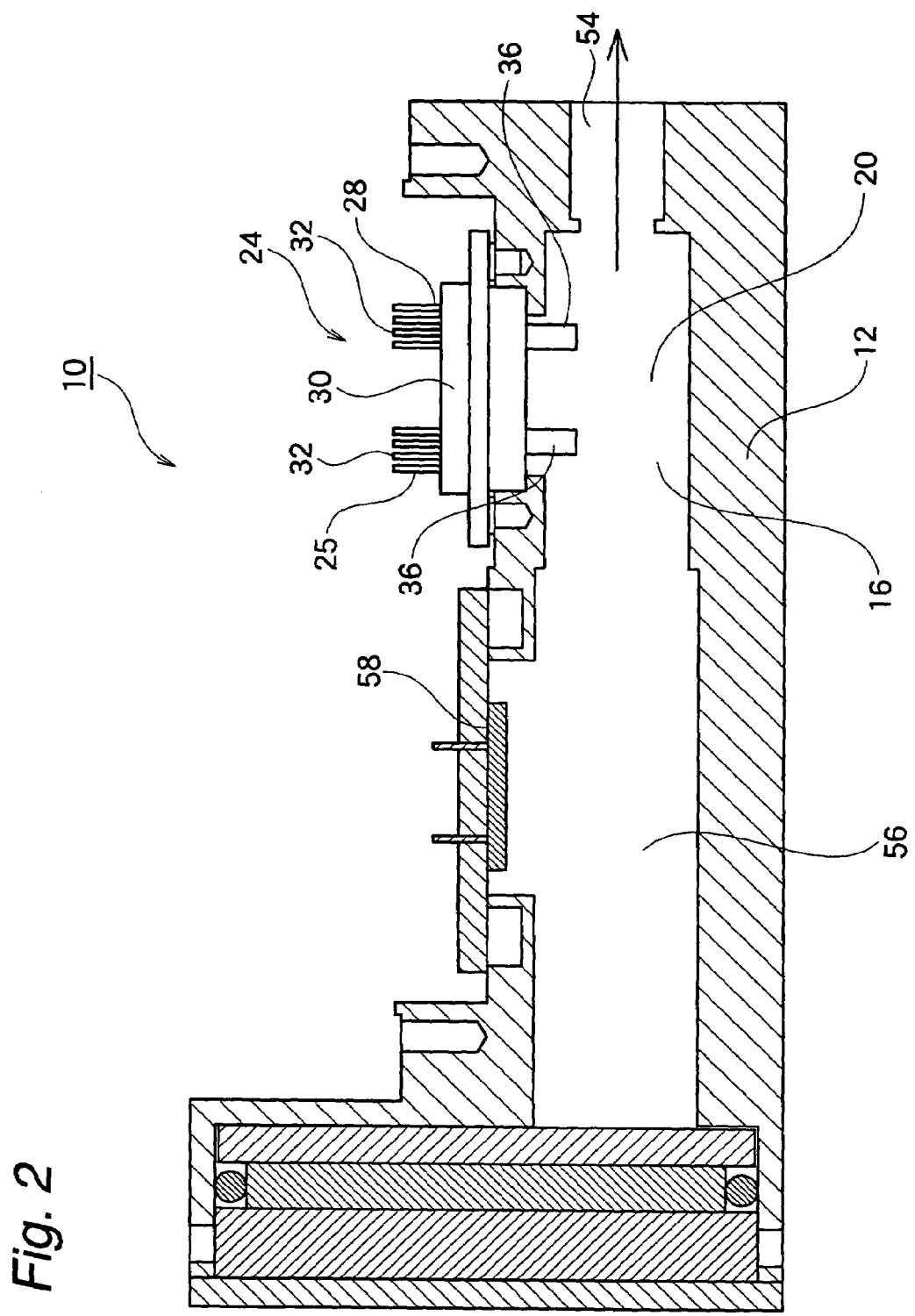
FIG. 2 is a sectional view taken along an A—A line in FIG. 1.
Figure 3:
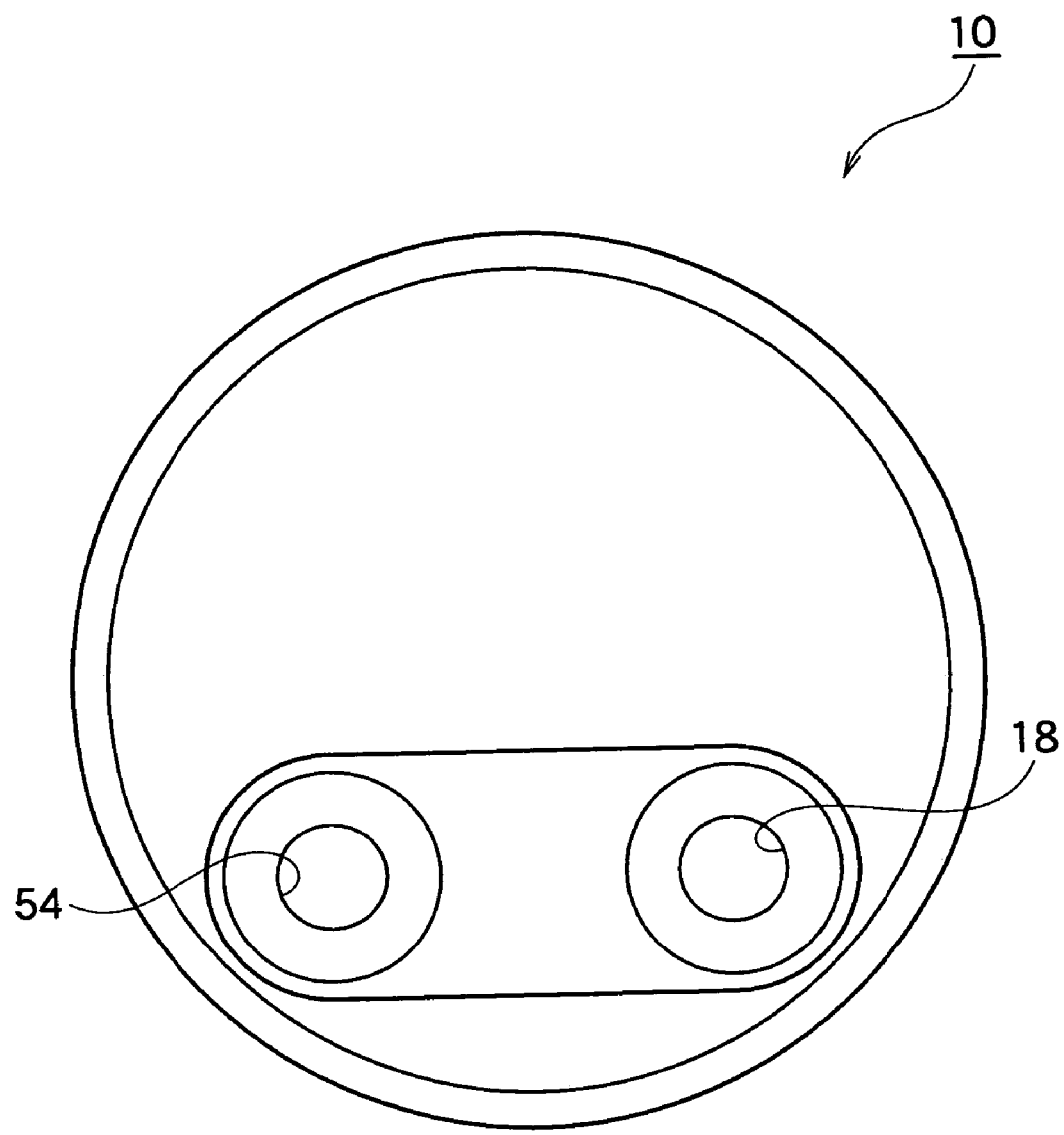
FIG. 3 is a right side view of FIG. 1.
Figure 4:
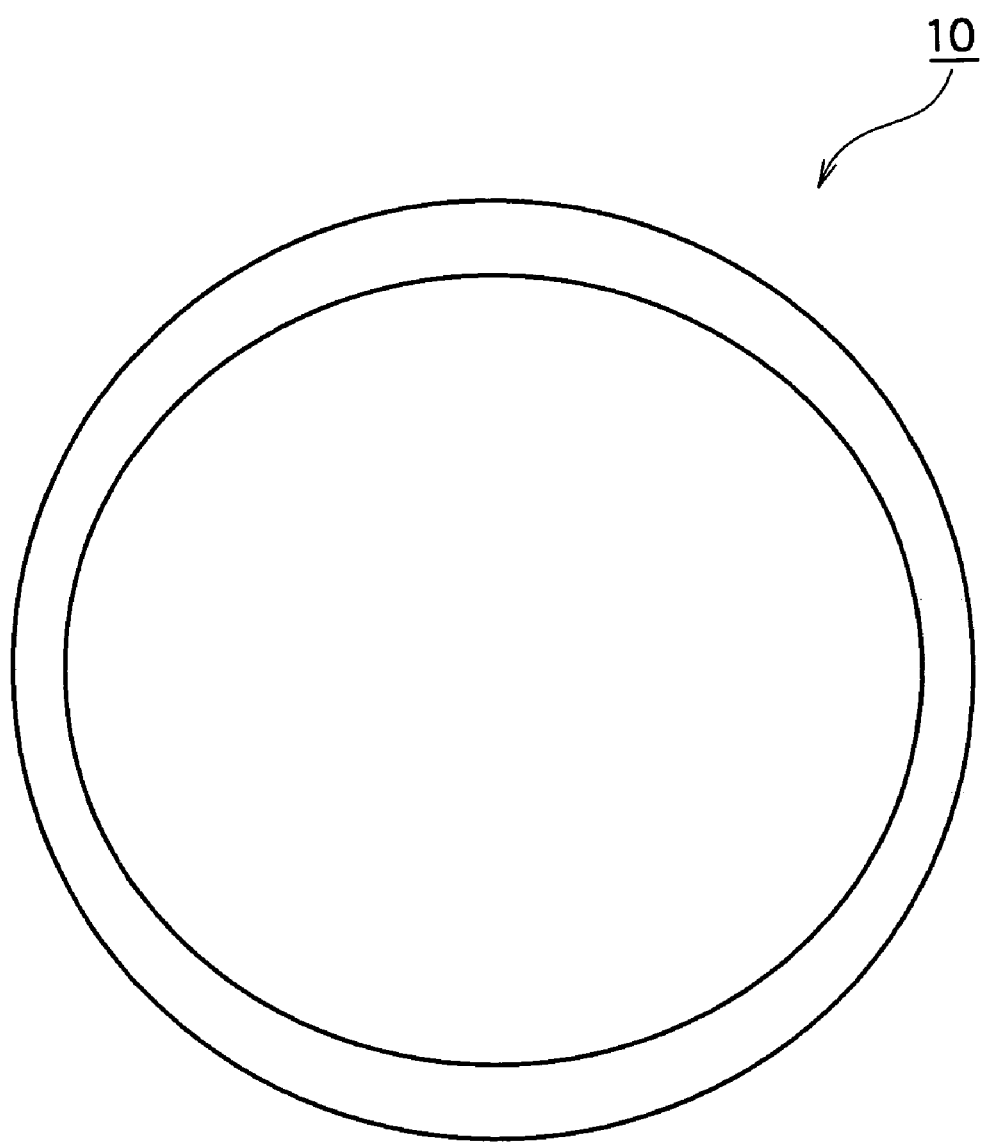
FIG. 4 is a left side view of FIG. 1.

As shown in FIGS. 1 and 2, an apparatus 10 for identifying the liquid type of a gasoline according to the present invention comprises a liquid type identifying apparatus body 12, and a first passage 14 and a second passage 16 which are formed in the liquid type identifying apparatus body 12.

As shown in an arrow of FIG. 1, a gasoline to be identified which flows from a gasoline inlet 18 into the first passage 14 passes through an alcoholic contents detecting chamber 56. Then, the identified gasoline passes through the alcoholic contents detecting chamber 56, and thereafter enters the second passage 16 to temporarily stay in a gasoline liquid type identifying chamber 20. The gasoline liquid type identifying chamber 20 is provided with an opening portion 22 for a liquid type identifying sensor taking the shape of a race track, positioned in an upper part thereof.

As shown in FIG. 2, a liquid type identifying sensor 24 is attached to the opening portion 22 for the liquid type identifying sensor.

Figure 5:
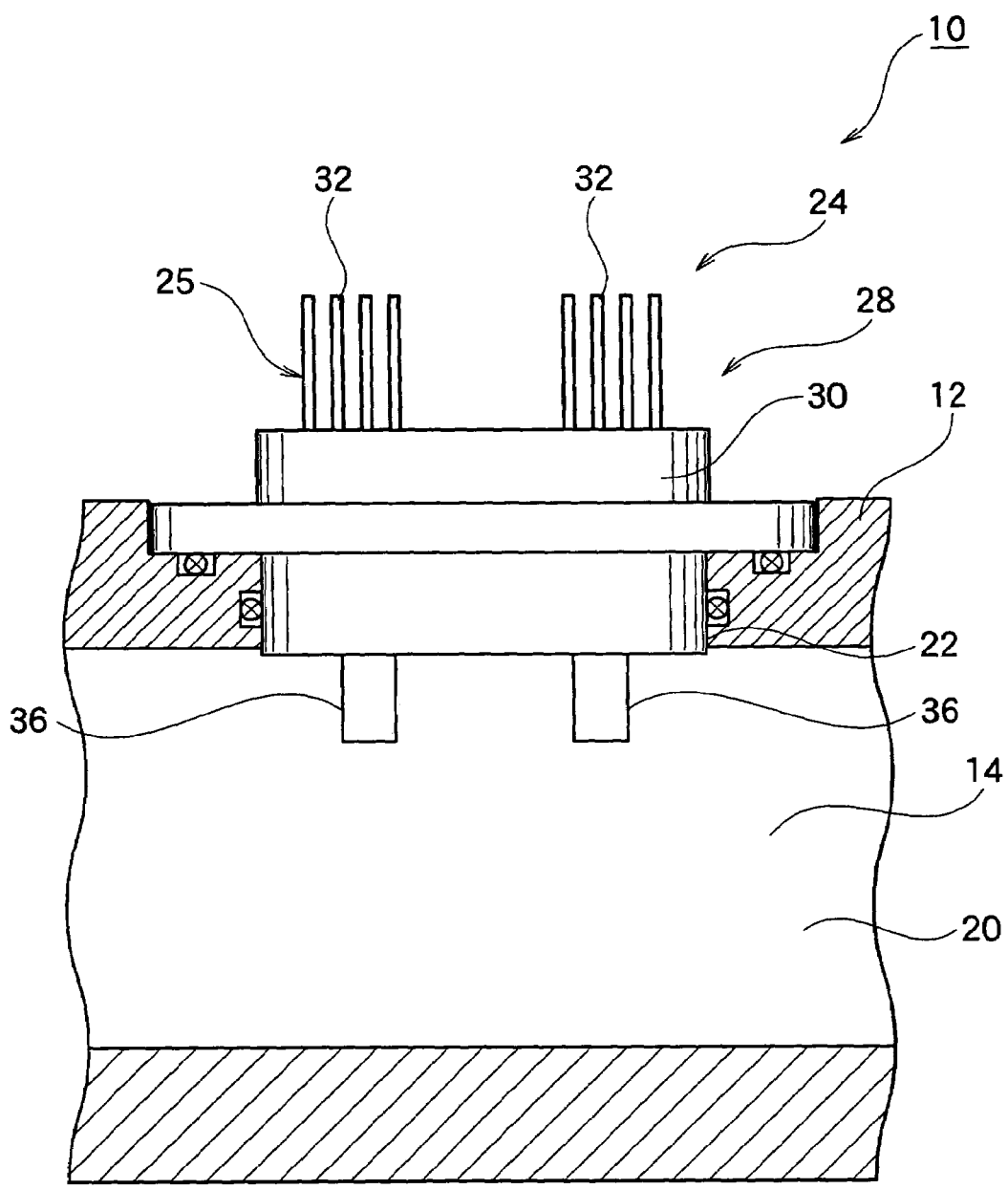
FIG. 5 is a partially enlarged sectional view showing a state in which a liquid type identifying sensor is attached in FIG. 2.

As shown in FIG. 5, the liquid type identifying sensor 24 includes a liquid type identifying sensor heater 25 and a liquid temperature sensor 28 provided apart from the liquid type identifying sensor heater 25 at a constant interval. The liquid type identifying sensor heater 25 and the liquid temperature sensor 28 are formed integrally by a mold resin 30.

Figure 6:
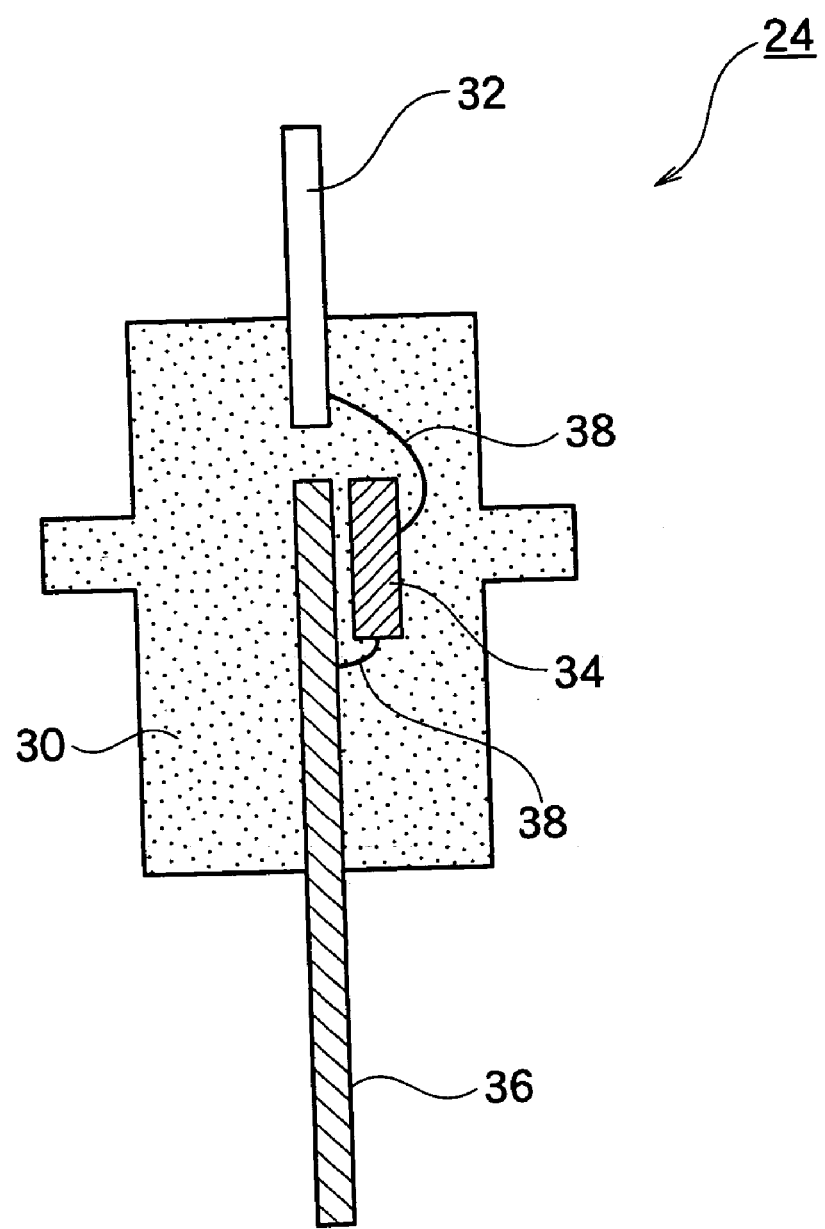
FIG. 6 is a sectional view showing the liquid type identifying sensor.

As shown in FIG. 6, moreover, the liquid type identifying sensor heater 25 includes a lead electrode 32 and a thin film chip portion 34. Moreover, the liquid type identifying sensor heater 25 is provided with a metallic fin 36 protruded into the gasoline liquid type identifying chamber 20 to directly come in contact with the identified gasoline through the opening portion 22 for the liquid type identifying sensor from the mold resin 30. The lead electrode 32, the thin film chip portion 34 and the fin 36 are mutually connected electrically through a bonding wire 38.

On the other hand, the liquid temperature sensor 28 also has the same structure as that of the liquid type identifying sensor heater 25, and includes the lead electrode 32, the thin film chip portion 34, the fin 36 and the bonding wire 38 respectively.

Figure 7:
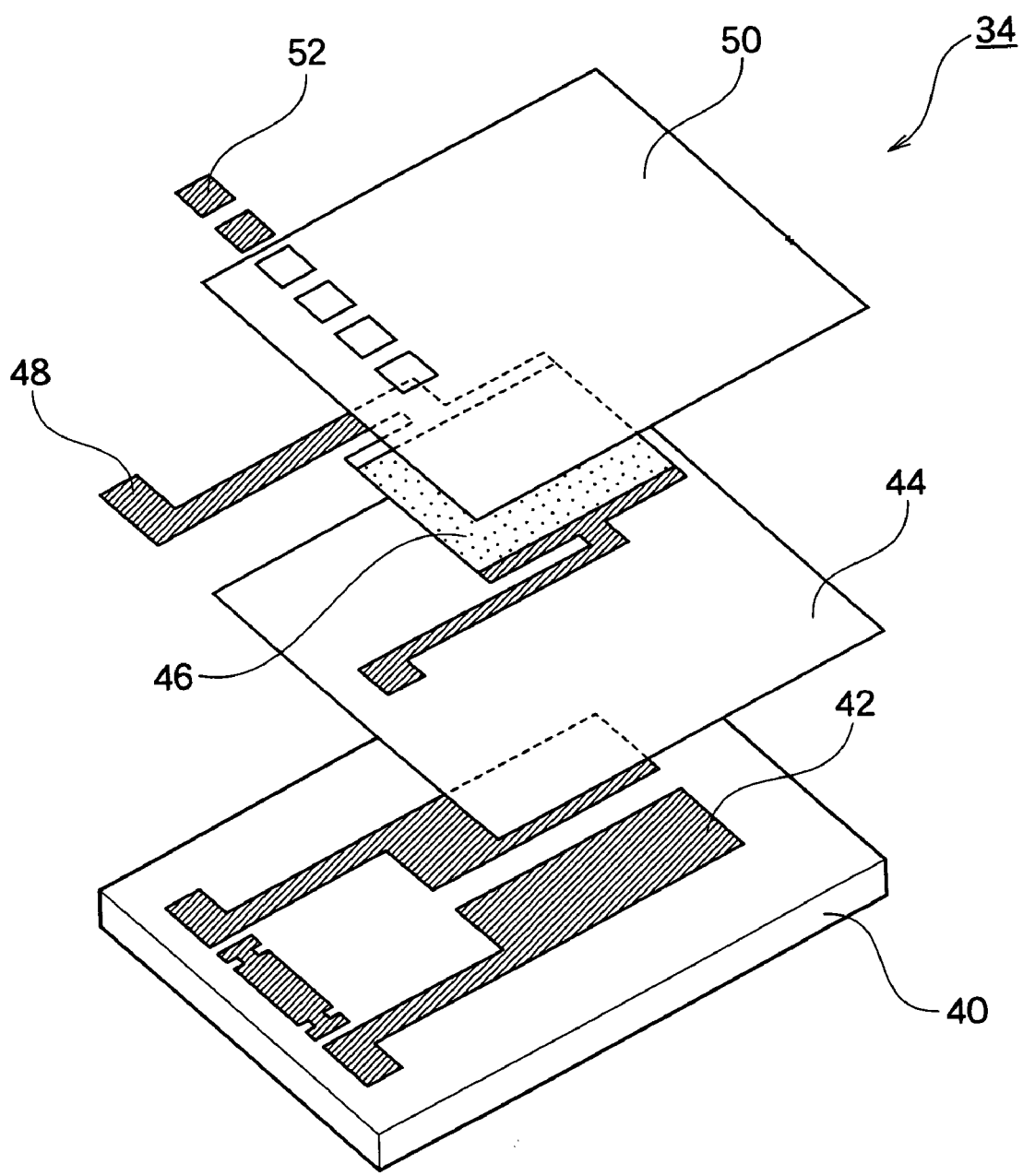
FIG. 7 is a partially enlarged exploded perspective view showing a state in which the thin film chip portions of the liquid type identifying sensor are laminated.

As shown in FIG. 7, the thin film chip portion 34 is constituted by a thin film-shaped chip in which a substrate 40 formed of $Al_2O_3$, a temperature sensor (temperature detector) 42 formed of PT, an interlayer insulating film 44 formed of $SiO_2$, a heater (heating member) 46 formed of $TaSiO_2$, a heating member electrode 48 formed of Ni, a protective film 50 formed of $SiO_2$, and an electrode pad 52 formed of Ti/Au are provided in order, for example.

While the thin film chip portion 34 of the liquid temperature sensor 28 also has the same structure, it is so constituted as not to cause the heater (heating member) 46 to act but to cause only the temperature sensor (temperature detector) 42 to act.

After the liquid type of the identified gasoline is identified by the liquid type identifying sensor 24, the identified gasoline is discharged from the gasoline liquid type identifying chamber 20 to an outside through a gasoline discharge port 54.

On the other hand, the identified gasoline flowing into the first passage 14 through the gasoline inlet 18 then stays temporarily in the alcoholic contents detecting chamber 56. In this state, alcoholic contents are detected by an alcohol detecting sensor 58 when the gasoline contains alcohol. Thereafter, the same gasoline is discharged from the alcohol contents detecting chamber 56 through the gasoline discharge port 54 of the second passage 16. The details of the detection of the alcohol will be omitted in the present example.

In FIGS. 1 and 2, moreover, circuit board members connected to the liquid type identifying sensor 24 and the alcohol detecting sensor 58 and lid members for covering them are not shown.

Figure 8:
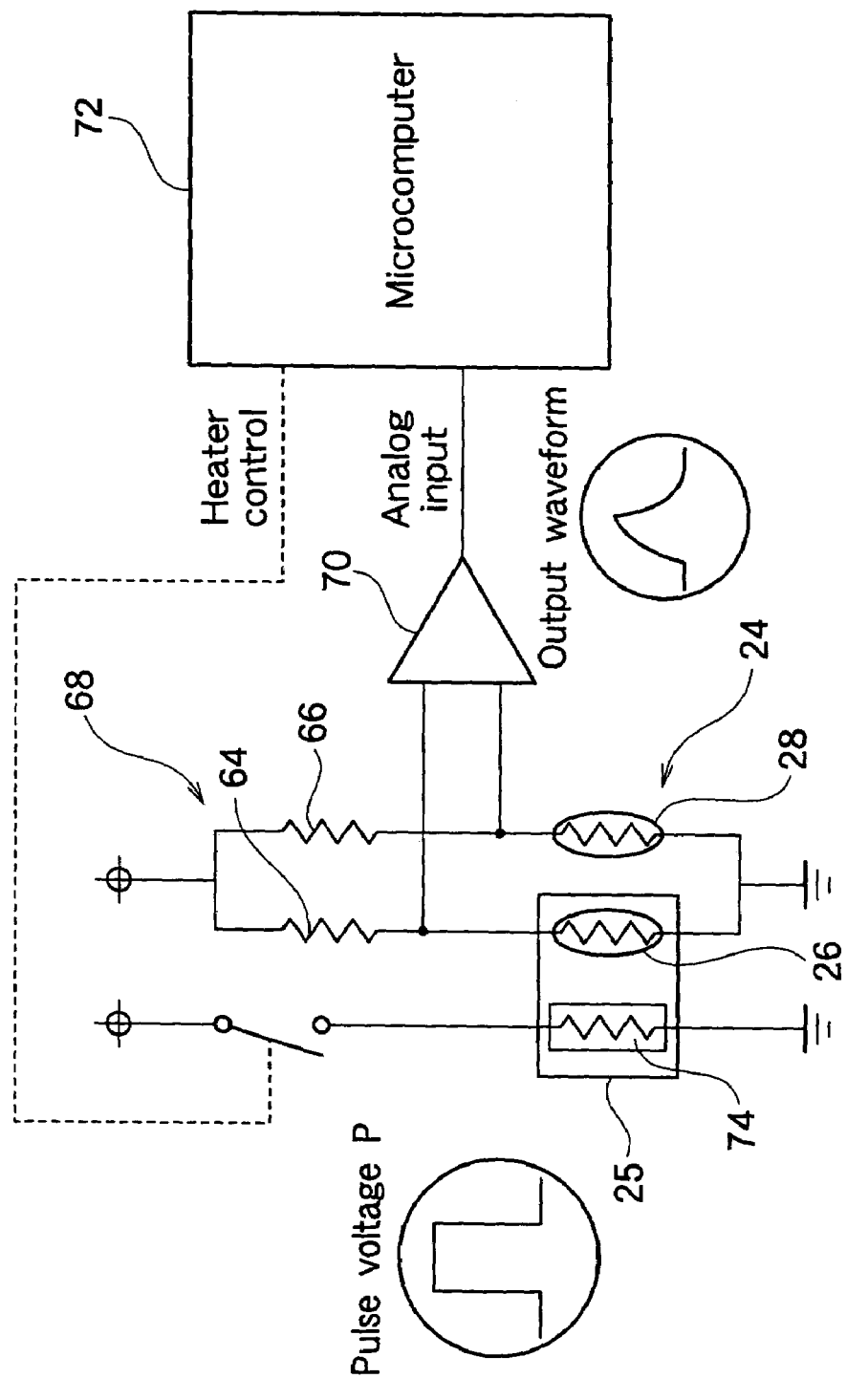
FIG. 8 is a schematic diagram showing the structure of a circuit according to the example of the apparatus for identifying the liquid type of a gasoline according to the present invention.

The apparatus 10 for identifying the liquid type of a gasoline according to the present invention has the structure of a circuit shown in FIG. 8.

In FIG. 8, an identifying liquid temperature sensor 26 of the liquid type identifying sensor heater 25 and the liquid temperature sensor 28 in the liquid type identifying sensor 24 are connected to each other through two resistors 64 and 66, thereby constituting a bridge circuit 68. The output of the bridge circuit 68 is connected to the input of an amplifier 70, and the output of the amplifier 70 is connected to the input of a computer 72 constituting an identification control portion.

Moreover, the applied voltage of a heater 74 of the liquid type identifying sensor heater 25 is controlled under the control of the computer 72.

In the apparatus 10 for identifying the liquid type of a gasoline which has such a structure, the liquid type of the gasoline is identified in the following manner.

First of all, the identified gasoline is caused to flow from the gasoline inlet 18 of the first passage 14 of the apparatus 10 for identifying the liquid type of a gasoline and is caused to stay temporarily in the gasoline liquid type identifying chamber 20 of the second passage 16.

Figure 9:
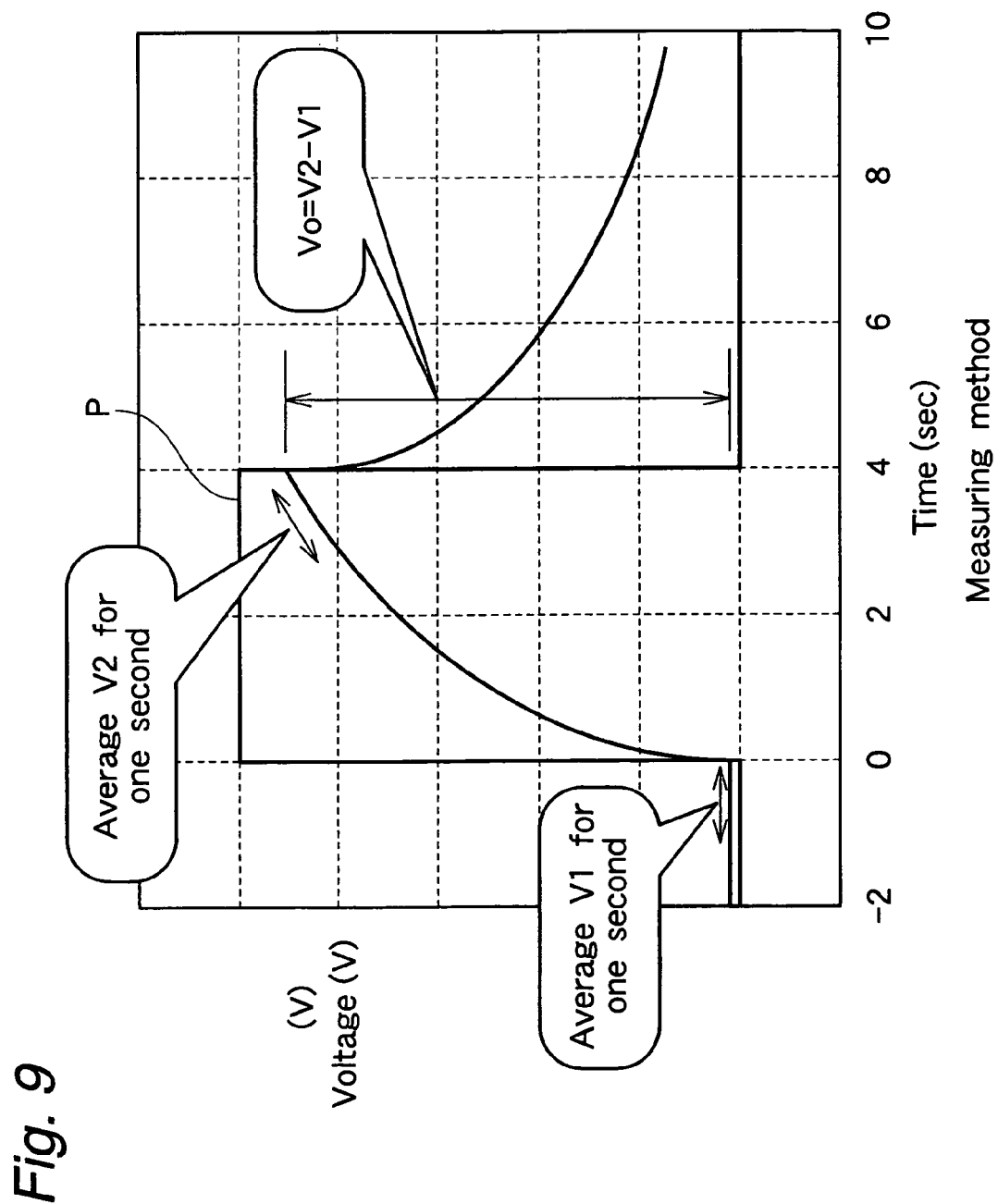
FIG. 9 is a graph showing a relationship between a time and a voltage, illustrating a method for identifying a liquid type using the apparatus for identifying the liquid type of a gasoline according to the present invention.

As shown in FIGS. 8 and 9, a pulse voltage P is applied to the heater 74 of the liquid type identifying sensor heater 25 under the control of the computer 72 for a predetermined time, that is, four seconds in the present example. Then, a change in the temperature of the analog output of a sensing portion, that is, the sensor bridge circuit 68 shown in FIG. 8 is measured.

More specifically, as shown in FIG. 9, the voltage difference of the sensor bridge circuit 68 is sampled at a predetermined number of times, for example, 256 times in the present example for one second before the pulse voltage P is applied to the heater 74 of the liquid type identifying sensor heater 25, and an average value thereof is set to be an average initial voltage V1. The value of the average initial voltage V1 corresponds to the initial temperature of the identifying liquid temperature sensor 26.

As shown in FIG. 9, the predetermined pulse voltage P, that is, a voltage of 10V in the present example is applied to the heater 74 of the liquid type identifying sensor heater 25 for four seconds. Subsequently, a value obtained by sampling a peak voltage at a predetermined number of times, for example, 256 times in the present example for one second after a predetermined time, for example, 3 seconds in the present example is set to be an average peak voltage V2. The average peak voltage V2 corresponds to the peak temperature of the identifying liquid temperature sensor 26.

A voltage output difference V0 is obtained from a voltage difference between the average initial voltage V1 and the average peak voltage V2, that is, $$V0=V2-V1.$$

Figure 10:
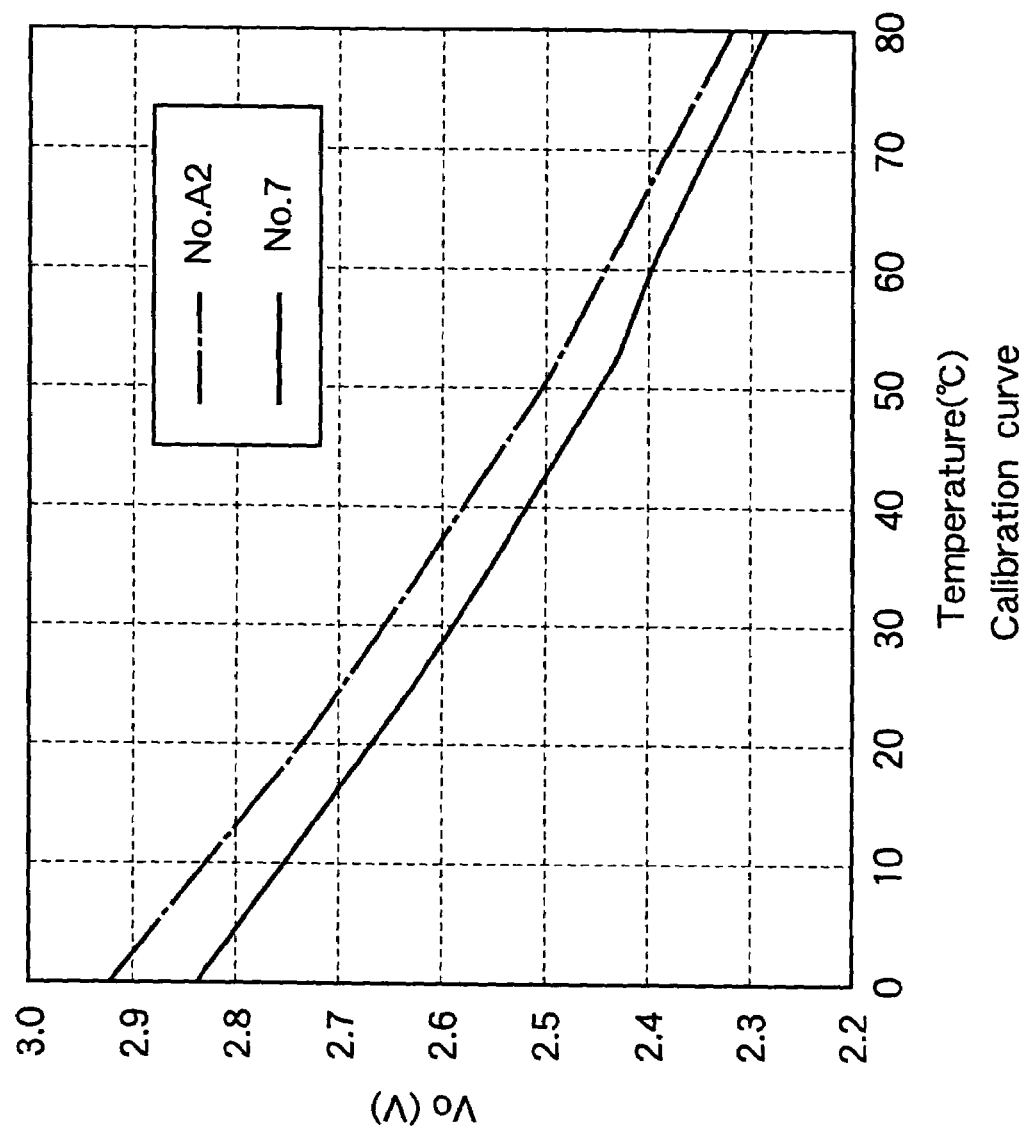
FIG. 10 is a graph showing a calibration curve, illustrating the method for identifying a liquid type using the apparatus for identifying the liquid type of a gasoline according to the present invention.

By such a method, as shown in FIG. 10, calibration curve data to be the correlation of a voltage output difference with a temperature are previously obtained for a predetermined reference gasoline, that is, the heaviest gasoline A2 (which rarely evaporates) and the lightest gasoline No. 7 (which easily evaporates) in the present example. The obtained calibration curve data are stored in the computer 72 constituting the identification control portion.

Based on the calibration curve data, a proportional calculation is carried out in the computer 72 and the type of the gasoline is identified with the voltage-output difference V0 obtained for the identified gasoline.

Figure 11:
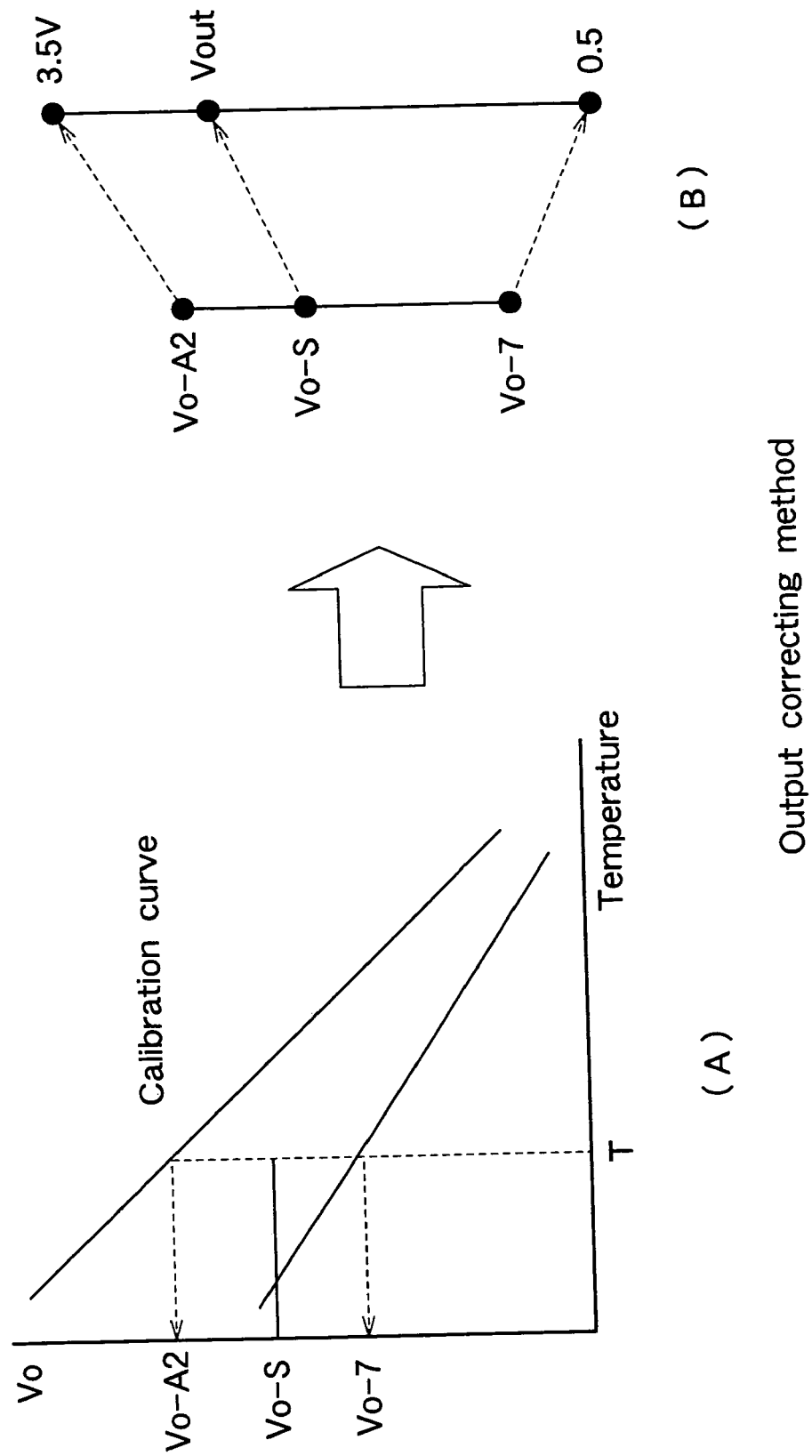
FIG. 11 is a graph showing an output correcting method in the method for identifying a liquid type using the apparatus for identifying the liquid type of a gasoline according to the present invention.

More specifically, as shown in FIG. 11, a liquid type voltage output Vout for the voltage output difference V0 at a measuring temperature T of the identified gasoline is correlated with an output voltage for a voltage output difference at a measuring temperature for a predetermined threshold reference gasoline (the gasoline A2 and the gasoline No. 7 in the present example) and is thus corrected.

In other words, as shown in FIG. 11(A), a voltage output difference V0–A2 of the gasoline A2, a voltage output difference V0–7 of the gasoline No. 7 and a voltage output difference V0–S of the identified gasoline are obtained at the temperature T based on the calibration curve data.

As shown in FIG. 11(B), the liquid type voltage output Vout of the identified gasoline is obtained by setting the liquid type output of the threshold reference gasoline in this case to have a predetermined voltage, that is, by setting the liquid type output of the gasoline A2 to be 3.5V and the liquid type output of the gasoline No. 7 to be 0.5V in the present example. Thus, a correlation with the characteristics of the gasoline can be acquired.

The liquid type voltage output Vout of the identified gasoline is compared with data previously stored in the computer 72 based on the calibration curve data. Consequently, it is possible to identify the liquid type of the gasoline accurately and rapidly (instantaneously).

The method for identifying the liquid type of a gasoline described above utilizes a natural convection and a principle in which the kinetic viscosity of the gasoline and the sensor output have a correlation.

In such a method for identifying the liquid type of a gasoline, moreover, it is apparent that a greater correlation is obtained with distillation characteristics T30 to T70 of the gasoline shown in FIG. 15, which is desirable.

Figure 12:
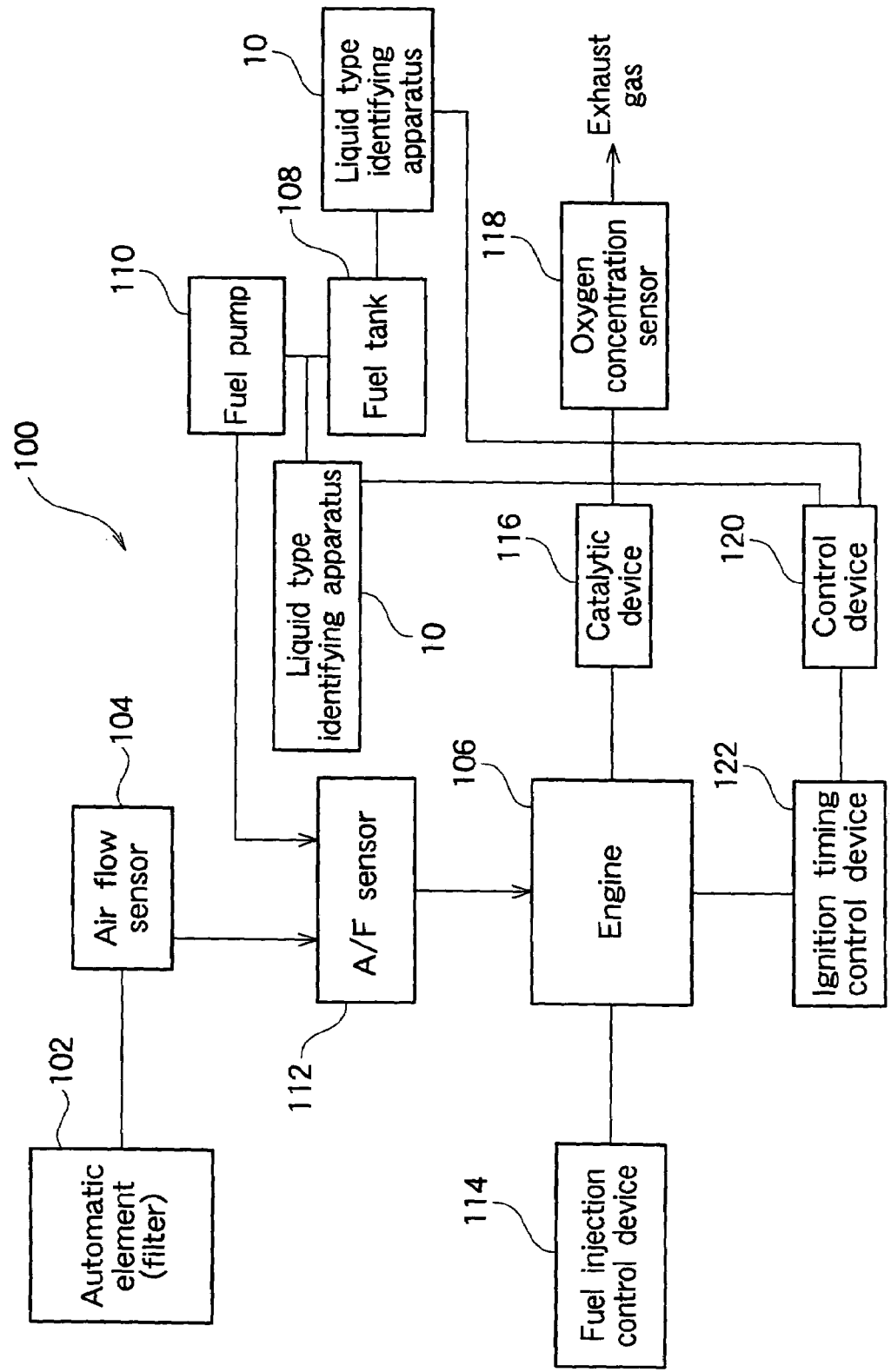
FIG. 12 is the same schematic diagram as FIG. 14, illustrating an example in which an apparatus 10 for identifying the liquid type of a gasoline according to the present invention is applied to a car system.
Figure 14:
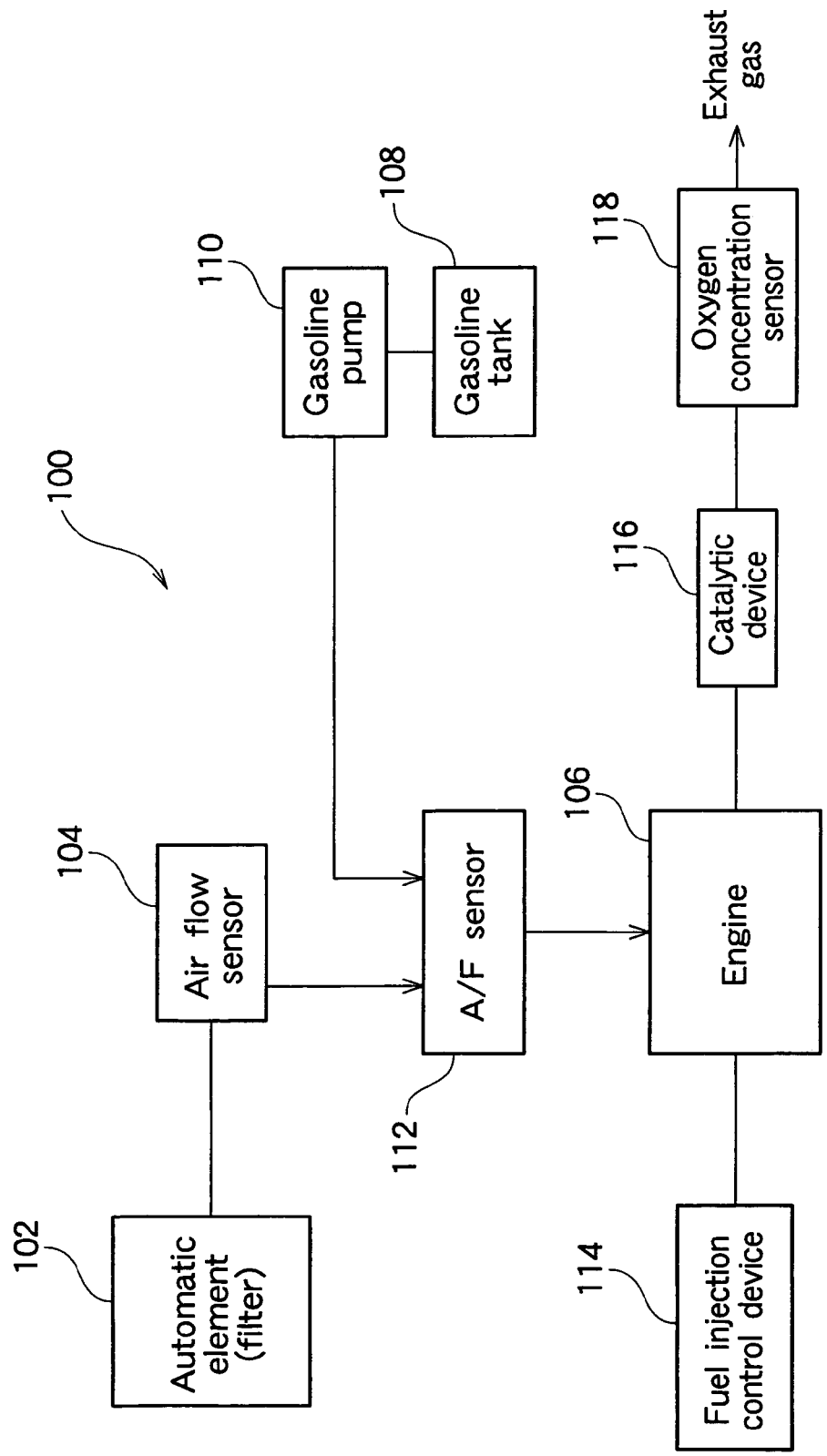
FIG. 14 is a schematic diagram showing a conventional car system.

FIG. 12 is the same schematic diagram as FIG. 14, illustrating an example in which the apparatus 10 for identifying the liquid type of a gasoline having such a structure is applied to a car system.

The same components as those in FIG. 14 have the same reference numerals and detailed description thereof will be omitted.

In a car system 100, the apparatus 10 for identifying the liquid type of a gasoline is provided in a gasoline tank 108 or on the upstream side of a gasoline pump 110.

The apparatus 10 for identifying the liquid type of a gasoline identifies the liquid type of a gasoline in the gasoline tank 108 or on the upstream or downstream side of the gasoline pump 110 (the case of the upstream side will be described in the present example for convenience of explanation). Then, the apparatus 10 regulates an ignition timing by an ignition timing control device 122 under the control of a control device 120 depending on the type of the gasoline.

More specifically, in the case in which the light gasoline No. 7 (which easily evaporates) is identified, for example, the ignition timing is controlled to be quickened. To the contrary, in the case in which the heavy gasoline A2 (which rarely evaporates) is identified, the ignition timing is controlled to be delayed.

Consequently, it is also possible to reduce the amount of HC in an exhaust gas and to enhance a mileage without decreasing a torque, particularly, at time of engine starting in which an engine and a catalytic device do not warm up.

Figure 13:
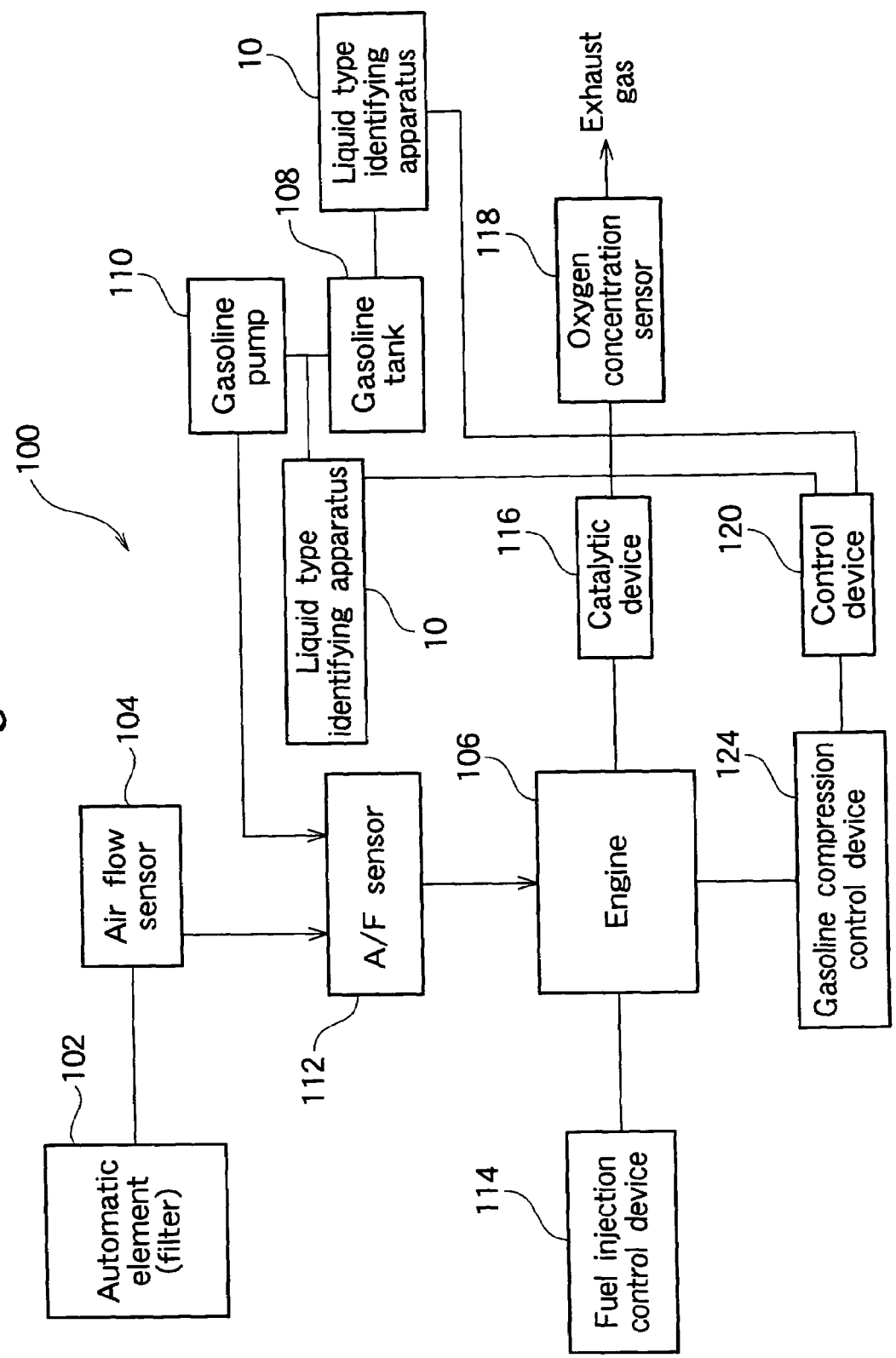
FIG. 13 is the same schematic diagram as FIG. 14, illustrating an example in which the apparatus 10 for identifying the liquid type of a gasoline according to the present invention is applied to the car system.

FIG. 13 is the same schematic diagram as FIG. 14, illustrating an example in which the apparatus 10 for identifying the liquid type of a gasoline having such a structure is applied to a car system.

The same components as those in FIG. 14 have the same reference numerals and detailed description thereof will be omitted.

In a car system 100, the apparatus 10 for identifying the liquid type of a gasoline is provided in a gasoline tank 108 or on the upstream side of a gasoline pump 110.

The apparatus 10 for identifying the liquid type of a gasoline identifies the liquid type of a gasoline in the gasoline tank 108 or on the upstream or downstream side of the gasoline pump 110 (the case of the upstream side will be described in the present example for convenience of explanation). Then, the apparatus 10 regulates the compressibility of the gasoline by a gasoline compression control device 124 under the control of a control device 120 depending on the type of the gasoline.

More specifically, in the case in which the light gasoline No. 7 (which easily evaporates) is identified, for example, the compressibility is controlled to be reduced. To the contrary, in the case in which the heavy gasoline A2 (which rarely evaporates) is identified, the compressibility is controlled to be increased.

Consequently, it is also possible to reduce the amount of HC in an exhaust gas and to enhance a mileage without decreasing a torque, particularly, at time of engine starting in which an engine and a catalytic device do not warm up.

While the preferred examples of the present invention have been described above, the present invention is not restricted thereto but various changes can be made without departing from the objects of the present invention, for example, a pulse voltage P, the number of sampling operations and the like can be changed properly.

According to the present invention, it is sufficient that a pulse voltage is applied for a predetermined time. Consequently, it is possible to identify the type of a gasoline accurately and rapidly through heating for a short time without carrying out the heating to such a temperature as to ignite the gasoline.

More specifically, there are utilized the correlation of the kinetic viscosity of the gasoline with a sensor output, a natural convection, and furthermore, an applied voltage having one pulse. Therefore, it is possible to identify the type of the gasoline accurately and rapidly.

According to the present invention, moreover, it is possible to accurately obtain a voltage output difference V0 based on the average value of sampling at a predetermined number of times for the applied voltage having one pulse. Consequently, it is possible to identify the type of the gasoline accurately and rapidly.

According to the present invention, furthermore, the type of the gasoline is identified with the voltage output difference V0 obtained for the identified gasoline, based on calibration curve data to be the correlation of a voltage output difference with a temperature for a predetermined reference gasoline which is prestored. Therefore, it is possible to identify the type of the gasoline more accurately and rapidly.

According to the present invention, moreover, a liquid type voltage output Vout for the voltage output difference V0 at the measuring temperature of the identified gasoline is correlated with the output voltage for the voltage output difference at the measuring temperature for a predetermined threshold reference gasoline and is thus corrected. Consequently, it is possible to eliminate the influence of the temperature on the voltage output difference V0, thereby giving the correlation of the liquid type voltage output Vout with the characteristics of the gasoline more accurately. Thus, it is possible to identify the type of the gasoline further accurately and rapidly.

According to the present invention, furthermore, a mechanism portion for carrying out a mechanical operation is not present. Therefore, an operation failure is not caused by a deterioration with the passage of time, foreign matters in the gasoline or the like. Thus, it is possible to identify the liquid type of the gasoline accurately and rapidly.

In addition, the sensor portion can be constituted to be very small-sized. Consequently, it is possible to identify the liquid type of the gasoline accurately with a very excellent thermal responsiveness.

According to the present invention, moreover, the heater of the liquid type identifying sensor heater, the identifying liquid temperature sensor and the liquid temperature sensor do not directly come in contact with the identified gasoline. Therefore, an operation failure is not caused by a deterioration with the passage of time, foreign matters in the gasoline or the like. Thus, it is possible to identify the liquid type of the gasoline accurately and rapidly.

According to the present invention, furthermore, it is possible to identify the type of the gasoline in a car accurately and rapidly and to regulate an ignition timing based on the result of the identification of the type of the gasoline.

Consequently, it is possible to obtain a proper ignition timing depending on the type of the gasoline.

According to the present invention, furthermore, it is possible to identify the type of the gasoline in a car accurately and rapidly and to regulate the compressibility of the gasoline based on the result of the identification of the type of the gasoline.

Consequently, it is possible to obtain a proper compressibility of the gasoline depending on the type of the gasoline.

Therefore, it is also possible to reduce the amount of HC in an exhaust gas and to enhance a mileage without decreasing a torque, particularly, at time of engine starting in which an engine and a catalytic device do not warm up. Thus, the present invention can produce various remarkable and peculiar functions and effects, which is very excellent.

The invention claimed is:

1. An apparatus for identifying a liquid type of a gasoline, comprising:
a gasoline liquid type identifying chamber for causing an identified gasoline introduced into a liquid type identifying apparatus body to stay temporarily;
a liquid type identifying sensor heater provided in the gasoline liquid type identifying chamber; and
a liquid temperature sensor provided in the gasoline liquid type identifying chamber apart from the liquid type identifying sensor heater at a constant interval,
the liquid type identifying sensor heater including a heater and an identifying liquid temperature sensor provided in the vicinity of the heater, and
the apparatus further comprising an identification control portion;
the identification control portion being constructed so that a pulse voltage is applied to the liquid type identifying sensor heater for a predetermined time, and the identified gasoline staying temporarily in the gasoline liquid type identifying chamber is heated by the heater and the liquid type is identified with a voltage output difference (V0) corresponding to a temperature difference between an initial temperature and a peak temperature in the identifying liquid temperature sensor.

2. The apparatus for identifying a liquid type of a gasoline according to claim 1, wherein the voltage output difference (V0) is equal to a voltage difference between an average initial voltage (V1) obtained by sampling an initial voltage before application of the pulse voltage at a predetermined number of times and an average peak voltage (V2) obtained by sampling a peak voltage after the application of the pulse voltage at a predetermined number of times, that is, $$V0=V2-V1.$$

3. The apparatus for identifying a liquid type of a gasoline according to claim 1, wherein the identification control portion identifies a type of a gasoline with the voltage output difference (V0) obtained for the identified gasoline, which is based on calibration curve data to be a correlation of a voltage output difference with a temperature for a predetermined reference gasoline prestored in the identification control portion.

4. The apparatus for identifying a liquid type of a gasoline according to claim 1, wherein the identification control portion correlates a liquid type voltage output (Vout) for the voltage output difference (V0) at a measuring temperature of the identified gasoline with an output voltage for a voltage output difference at a measuring temperature for a predetermined threshold reference gasoline and thus carries out a correction.

5. The apparatus for identifying a liquid type of a gasoline according to claim 1, wherein the liquid type identifying sensor heater is a laminated liquid type identifying sensor heater in which a heater and an identifying liquid temperature sensor are laminated through an insulating layer.

6. The apparatus for identifying a liquid type of a gasoline according to claim 1, wherein the heater and the identifying liquid temperature sensor in the liquid type identifying sensor heater are constituted to come in contact with the identified gasoline through a metallic fin, respectively.

7. The apparatus for identifying a liquid type of a gasoline according to claim 1, wherein the liquid temperature sensor is constituted to come in contact with the identified gasoline through a metallic fin.

8. A method for identifying a liquid type of a gasoline, comprising the steps of:
applying a pulse voltage for a predetermined time to a liquid type identifying sensor heater including a heater and an identifying liquid temperature sensor provided in the vicinity of the heater;
heating an identified gasoline by the heater; and
identifying the liquid type with a voltage output difference (V0) corresponding to a temperature difference between an initial temperature and a peak temperature in the identifying liquid temperature sensor.

9. The method for identifying a liquid type of a gasoline according to claim 8, wherein the voltage output difference (V0) is equal to a voltage difference between an average initial voltage (V1) obtained by sampling an initial voltage before application of the pulse voltage at a predetermined number of times and an average peak voltage (V2) obtained by sampling a peak voltage after the application of the pulse voltage at a predetermined number of times, that is, $$V0=V2-V1.$$

10. The method for identifying a liquid type of a gasoline according to claim 8, wherein a type of a gasoline is identified with the voltage output difference (V0) obtained for the identified gasoline, based on calibration curve data to be a correlation of a voltage output difference with a temperature for a predetermined reference gasoline which is prestored.

11. The method for identifying a liquid type of a gasoline according to claim 8, wherein a liquid type voltage output (Vout) for the voltage output difference (V0) at a measuring temperature of the identified gasoline is correlated with an output voltage for a voltage output difference at a measuring temperature for a predetermined threshold reference gasoline and is thus corrected.

12. The method for identifying a liquid type of a gasoline according to claim 8, wherein the liquid type identifying sensor heater is a laminated liquid type identifying sensor heater in which a heater and an identifying liquid temperature sensor are laminated through an insulating layer.

13. The method for identifying a liquid type of a gasoline according to claim 8, wherein the heater and the identifying liquid temperature sensor in the liquid type identifying sensor heater are constituted to come in contact with the identified gasoline through a metallic fin, respectively.

14. The method for identifying a liquid type of a gasoline according to claim 8, wherein the liquid temperature sensor is constituted to come in contact with the identified gasoline through a metallic fin.

15. An apparatus for identifying a liquid type of a gasoline of a car, comprising:

the apparatus for identifying a liquid type of a gasoline according to claim 1 which is provided in one of a gasoline tank, or on an upstream side or a downstream side of a gasoline pump.

16. A method for identifying a liquid type of a gasoline of a car, comprising the step of:
  identifying a type of a gasoline in a gasoline tank or on an upstream side or a downstream side of a gasoline pump by using the method for identifying a liquid type of a gasoline according to claim 8.

17. An apparatus for reducing an exhaust gas of a car, comprising:
  the apparatus for identifying a liquid type of a gasoline according to claim 1 which is provided in a gasoline tank or on an upstream side or a downstream side of a gasoline pump; and
  an ignition timing control device for regulating an ignition timing based on a type of the gasoline which is identified by the apparatus for identifying a liquid type of a gasoline.

18. A method for reducing an exhaust gas of a car comprising the steps of:
  identifying a type of a gasoline in a gasoline tank or on an upstream side or a downstream side of a gasoline pump by using the method for identifying a liquid type of a gasoline according to claim 8, and
  regulating an ignition timing based on the type of the gasoline which is identified by the apparatus for identifying a liquid type of a gasoline.

19. An apparatus for reducing an exhaust gas of a car, comprising:
  the apparatus for identifying a liquid type of a gasoline according to claim 1 which is provided in a gasoline tank or on an upstream side or a downstream side of a gasoline pump; and
  a gasoline compression control device for regulating a compressibility of the gasoline based on a type of the gasoline which is identified by the apparatus for identifying a liquid type of a gasoline.

20. A method for reducing an exhaust gas of a car, comprising the steps of:
  identifying a type of a gasoline in a gasoline tank or on an upstream side or a downstream side of a gasoline pump by using the method for identifying a liquid type of a gasoline according to claim 8, and regulating a compressibility of the gasoline based on the type of the gasoline which is identified by the apparatus for identifying a liquid type of a gasoline.

21. The apparatus for identifying a liquid type of a gasoline according to claim 2, wherein the identification control portion identifies a type of a gasoline with the voltage output difference (V0) obtained for the identified gasoline, which is based on calibration curve data to be a correlation of a voltage output difference with a temperature for a predetermined reference gasoline prestored in the identification control portion.

22. The apparatus for identifying a liquid type of a gasoline according to claim 2, wherein the identification control portion correlates a liquid type voltage output (Vout) for the voltage output difference (V0) at a measuring temperature of the identified gasoline with an output voltage for a voltage output difference at a measuring temperature for a predetermined threshold reference gasoline and thus carries out a correction.

23. The apparatus for identifying a liquid type of a gasoline according to claim 3, wherein the identification control portion correlates a liquid type voltage output (Vout) for the voltage output difference (V0) at a measuring temperature of the identified gasoline with an output voltage for a voltage output difference at a measuring temperature for a predetermined threshold reference gasoline and thus carries out a correction.

24. The method for identifying a liquid type of a gasoline according to claim 9, wherein a type of a gasoline is identified with the voltage output difference (V0) obtained for the identified gasoline, based on calibration curve data to be a correlation of a voltage output difference with a temperature for a predetermined reference gasoline which is prestored.

25. The method for identifying a liquid type of a gasoline according to claim 9, wherein a liquid type voltage output (Vout) for the voltage output difference (V0) at a measuring temperature of the identified gasoline is correlated with an output voltage for a voltage output difference at a measuring temperature for a predetermined reference gasoline and is thus corrected.

26. The method for identifying a liquid type of a gasoline according to claim 10, wherein a liquid type voltage output (Vout) for the voltage output difference (V0) at a measuring temperature of the identified gasoline is correlated with an output voltage for a voltage output difference at a measuring temperature for a predetermined threshold reference gasoline and is thus corrected.

27. An apparatus for identifying a liquid type of a gasoline of a car, comprising:
  the apparatus for identifying a liquid type of a gasoline according to claim 2 which is provided in one of a gasoline tank, or on an upstream side or a downstream side of a gasoline pump.

28. An apparatus for identifying a liquid type of a gasoline of a car, comprising:
  the apparatus for identifying a liquid type of a gasoline according to claim 3 which is provided in one of a gasoline tank, or on an upstream side or a downstream side of a gasoline pump.

29. An apparatus for identifying a liquid type of a gasoline of a car, comprising:
  the apparatus for identifying a liquid type of a gasoline according to claim 4 which is provided in one of a gasoline tank, or on an upstream side or a downstream side of a gasoline pump.

30. A method for identifying a liquid type of a gasoline of a car, comprising the step of:
  identifying a type of a gasoline in a gasoline tank or on an upstream side or a downstream side of a gasoline pump by using the method for identifying a liquid type of a gasoline according to claim 9.

31. A method for identifying a liquid type of a gasoline of a car, comprising the step of:
  identifying a type of a gasoline in a gasoline tank or on an upstream side or a downstream side of a gasoline pump by using the method for identifying a liquid type of a gasoline according to claim 10.

32. A method for identifying a liquid type of a gasoline of a car, comprising the step of:
  identifying a type of a gasoline in a gasoline tank or on an upstream side or a downstream side of a gasoline pump by using the method for identifying a liquid type of a gasoline according to claim 11.

33. An apparatus for reducing an exhaust gas of a car, comprising:
the apparatus for identifying a liquid type of a gasoline according to claim 2 which is provided in a gasoline tank or on an upstream side or a downstream side of a gasoline pump; and
an ignition timing control device for regulating an ignition timing based on a type of the gasoline which is identified by the apparatus for identifying a liquid type of a gasoline.

34. An apparatus for reducing an exhaust gas of a car comprising:
the apparatus for identifying a liquid type of a gasoline according to claim 3 which is provided in a gasoline tank or on an upstream side or a downstream side of a gasoline pump; and
an ignition timing control device for regulating an ignition timing based on a type of the gasoline which is identified by the apparatus for identifying a liquid type of a gasoline.

35. An apparatus for reducing an exhaust gas of a car, comprising:
the apparatus for identifying a liquid type of a gasoline according to claim 4 which is provided in a gasoline tank or on an upstream side or a downstream side of a gasoline pump; and
an ignition timing control device for regulating an ignition timing based on a type of the gasoline which is identified by the apparatus for identifying a liquid type of a gasoline.

* * * * *